(12) United States Patent
Gerder et al.

(10) Patent No.: US 11,491,271 B2
(45) Date of Patent: Nov. 8, 2022

(54) METHOD FOR CONTROLLING A DEVICE FOR EXTRACORPOREAL BLOOD GAS EXCHANGE, DEVICE FOR EXTRACORPOREAL BLOOD GAS EXCHANGE, AS WELL AS CONTROL DEVICE FOR CONTROLLING A DEVICE FOR EXTRACORPOREAL BLOOD GAS EXCHANGE

(71) Applicant: Drägerwerk AG & Co. KGaA, Lübeck (DE)

(72) Inventors: Henning Gerder, Lübeck (DE); Karsten Hiltawsky, Stockelsdorf (DE)

(73) Assignee: DRÄGER WERK AG & CO. KGAA, Lübeck (DE)

( * ) Notice: Subject to any disclaimer, the term of this patent is extended or adjusted under 35 U.S.C. 154(b) by 1087 days.

(21) Appl. No.: 15/845,025

(22) Filed: Dec. 18, 2017

(65) Prior Publication Data

US 2018/0169320 A1    Jun. 21, 2018

(30) Foreign Application Priority Data

Dec. 20, 2016   (DE) .................... 10 2016 015 122.6

(51) Int. Cl.
  *A61M 1/36*   (2006.01)
  *A61M 1/16*   (2006.01)
  *A61M 1/34*   (2006.01)

(52) U.S. Cl.
  CPC ........ *A61M 1/3639* (2013.01); *A61M 1/1601* (2014.02); *A61M 1/1698* (2013.01);
  (Continued)

(58) Field of Classification Search
  CPC ..... A61M 1/16; A61M 1/1601; A61M 1/1698
  See application file for complete search history.

(56) References Cited

U.S. PATENT DOCUMENTS 5,810,759 A   9/1998 Merz
7,435,226 B2  10/2008 Suarez
(Continued)

FOREIGN PATENT DOCUMENTS

DE   10 2013 012 433 A1   1/2015
DE   10 2014 009 439 A1   12/2015
(Continued)

OTHER PUBLICATIONS

Thomas Muders et al. "Tidal recruitment assessed by electrical impedance tomography and computed tomography in a porcine model of lung injury". Critical Care Medicine 2012, vol. 40, No. 3.

*Primary Examiner* — Leslie R Deak
(74) *Attorney, Agent, or Firm* — McGlew and Tuttle, P.C.

(57) ABSTRACT

A method controls a device for extracorporeal blood gas exchange. The device has a membrane as a gas-liquid barrier between a bloodstream and a gas stream. The membrane further makes possible a passing over of the carbon dioxide content from the bloodstream into the gas stream. The device has at least one actuator. A change in a value of an operating parameter of the actuator brings about a change in a value of the carbon dioxide content that passes over from the bloodstream into the gas stream. The method further includes providing breathing gas information that indicates a carbon dioxide concentration in breathing gas and providing a control signal, which indicates a request for setting a value of the operating parameter and changing of the value of the operating parameter as a function of the carbon dioxide concentration in the breathing gas.

15 Claims, 7 Drawing Sheets

(52) U.S. Cl.
CPC .......... *A61M 1/367* (2013.01); *A61M 1/3646*
(2014.02); *A61M 1/3652* (2014.02); *A61M*
*1/16* (2013.01); *A61M 1/3441* (2013.01);
*A61M 2205/3331* (2013.01)

(56) References Cited

U.S. PATENT DOCUMENTS

| | | | | |
|---|---|---|---|---|
| 8,720,441 | B2* | 5/2014 | Sinderby | A61M 16/021 |
| | | | | 128/204.23 |
| 9,384,549 | B2 | 7/2016 | Leonhardt et al. | |
| 2015/0030502 | A1 | 1/2015 | Gorhan et al. | |
| 2015/0034082 | A1* | 2/2015 | Kimm | A61B 5/4836 |
| | | | | 128/202.16 |
| 2016/0163062 | A1 | 6/2016 | Gärber | |
| 2016/0310069 | A1* | 10/2016 | Sinderby | A61B 5/7246 |
| 2016/0354007 | A1 | 12/2016 | Gärber | |
| 2017/0095601 | A1* | 4/2017 | Laubscher | A61M 16/0003 |
| 2019/0344005 | A1* | 11/2019 | Larsson | A61B 5/0488 |

FOREIGN PATENT DOCUMENTS

| | | |
|---|---|---|
| DE | 10 2014 018 107 A1 | 6/2016 |
| DE | 10 2015 006 902 B3 | 6/2016 |
| DE | 10 2015 015 296 A1 | 6/2017 |
| EP | 1 292 224 B1 | 11/2006 |
| WO | 2011 021 978 A1 | 2/2011 |

\* cited by examiner

METHOD FOR CONTROLLING A DEVICE FOR EXTRACORPOREAL BLOOD GAS EXCHANGE, DEVICE FOR EXTRACORPOREAL BLOOD GAS EXCHANGE, AS WELL AS CONTROL DEVICE FOR CONTROLLING A DEVICE FOR EXTRACORPOREAL BLOOD GAS EXCHANGE

CROSS REFERENCE TO RELATED APPLICATIONS

This application claims the benefit of priority under 35 U.S.C. § 119 of German Application 10 2016 015 122.6, filed Dec. 20, 2016, the entire contents of which are incorporated herein by reference.

FIELD OF THE INVENTION

Devices for extracorporeal blood gas exchange are known. Venous blood of a patient is hereby fed to such a device, which blood, after leaving the device, is then fed back again to the patient either via the artery of the patient or else either via the same vein or a different vein.

BACKGROUND OF THE INVENTION

Within the device, the bloodstream is fed through an area guiding the bloodstream along a membrane, which represents a gas-liquid barrier to a gas-guiding area. From the perspective of the bloodstream, a gas stream, which has the oxygen content, is located behind the membrane in the gas-guiding area. A blood gas exchange then takes place between the bloodstream and the gas stream by the carbon dioxide content of the bloodstream passing over through the membrane into the gas stream. Likewise, the oxygen content can pass over from the gas stream through the membrane into the bloodstream. As a result of this, two functions of the gas exchange are thus carried out, which functions shall be carried out in a human normally through normal breathing by means of the lung function. On the one hand, this is a removal of carbon dioxide from the blood and an enrichment of the blood with oxygen, on the other hand.

Such devices for extracorporeal blood gas exchange are especially used when a patient is not able to perform the blood gas exchange needed for his body alone via the lung or via breathing because of a reduced gas exchange via the lung.

If extracorporeal blood gas exchange is carried out by the respective access to the bloodstream via a vein taking place in both directions between the patient and the device, then typically only blood quantities of about 1-1.5 L/min can be treated.

However, if the blood is guided from an arterial access to the patient to the device and then from the device back to the patient via a venous access, then blood quantities on the magnitude of 3-4 L/min can be treated in an extracorporeal manner.

If both an arterial and a venous access are used, then the pressure difference between artery and vein can be used to let the bloodstream be delivered from the patient to the device and then back to the patient to the venous access independently, without having to provide an additional pumping capacity by means of an additional pump of the device. This is also known as a so-called pump-free extracorporeal lung assistance (pECLA).

However, if respective venous accesses at the patient are used both for feeding to and feeding back, then an additional pumping capacity by means of an additional pump of the device is always necessary to achieve the volume flow to be achieved.

A device for extracorporeal blood gas exchange usually has an oxygen source, wherein the value of the oxygen quantity that is present in the gas stream in the gas-guiding area can be changed via an actuator, for example, a valve at the oxygen source.

If the partial pressure of oxygen in the gas stream is higher than the partial pressure of oxygen in the bloodstream, then at least a certain percentage of the oxygen quantity of the gas stream passes over into the bloodstream. As a result of this, the extent of oxygen enrichment of the bloodstream can be controlled.

If the flow rate of the bloodstream along the membrane is increased, for example, by a pump for delivering the bloodstream, then removal of a larger quantity of carbon dioxide from the bloodstream into the gas stream takes place per unit of time. As a result, the extent of the removal of carbon dioxide from the bloodstream can thus be controlled.

Patients are frequently treated such that, in addition to using a device for extracorporeal blood gas exchange, the patient is also at the same time ventilated via a ventilator (also known as a respirator) or an anesthesia device in order not only to make possible a blood gas exchange via venous or arterial access, but also to make possible the blood gas exchange via the lung within the framework of breathing.

In principle, it is possible for clinicians to exert an influence on the extent to which the ventilator or the anesthesia device or else the device for extracorporeal blood gas exchange brings about a removal of carbon dioxide from the blood by performing settings at the ventilator and/or at the device for extracorporeal blood gas exchange. Such an interaction between the ventilator or anesthesia device and the device for extracorporeal blood gas exchange may also be called a so-called combined therapy.

SUMMARY OF THE INVENTION

An object of the present invention is to provide a method for controlling a device for extracorporeal blood gas exchange, in which an operating state of the device for extracorporeal blood gas exchange is controlled in such a way that the method assists a weaning of the patient from the extracorporeal removal of carbon dioxide.

Furthermore, an object of the present invention is to provide a device for extracorporeal blood gas exchange, which can be controlled via a data network interface with respect to an extent at which the carbon dioxide content passes over from the bloodstream into the gas stream.

Furthermore, an object of the present invention is to provide a device for extracorporeal blood gas exchange, wherein the device is itself controlled with respect to an extent at which the carbon dioxide content passes over from the bloodstream into the gas stream as a function of breathing gas information, which indicates a carbon dioxide concentration in a breathing gas.

Furthermore, an object of the present invention is to provide a control device for controlling a device for extracorporeal blood gas exchange, wherein the control device determines a carbon dioxide concentration in a breathing gas by means of a measuring unit and then provides a control signal to the device for extracorporeal blood gas exchange in order to influence an extent at which the carbon dioxide content passes over from the bloodstream into the gas stream, wherein the control device selects the control signal as a function of the carbon dioxide concentration in the breathing gas.

Furthermore, an object of the present invention is to provide a control device for controlling a device for extracorporeal blood gas exchange, wherein the control device can receive information about a carbon dioxide concentration in a breathing gas via a data signal and then provide a control signal for influencing the device for extracorporeal blood gas exchange with respect to an extent at which the carbon dioxide content passes over from the bloodstream into the gas stream, wherein the control device selects the control signal as a function of the information about the carbon dioxide concentration in the breathing gas.

The advantages of the method, of the devices for extracorporeal blood gas exchange as well as of the control devices are explained below in detail.

The present invention seizes the idea that in a so-called combined therapy of a patient using a ventilator or anesthesia device as well as a device for extracorporeal blood gas exchange, it may be a goal that the patient can be weaned from the extracorporeal removal of carbon dioxide from the blood with respect to the extracorporeal blood gas exchange or the extracorporeal removal of carbon dioxide from the blood in the course of a possibly ensuing recovery of his or her lung capacity or of his or her lung. Patients, who suffer, for example, from a lung disease in the form of COPD or of another impairment of the lung function, may possibly recover in the course of the treatment with respect to their lung function in the manner that the extent at which carbon dioxide can be removed from the blood via the lung into the breathing gas increases, as viewed over time, due to a recovery of the lung. While a blood gas exchange in an extracorporeal manner may thus possibly be vital at the start of the treatment, it may then be possible at a later time to reduce the breathing assistance due to the extracorporeal blood gas exchange. This is achieved according to the method according to the invention by taking into consideration breathing gas information, which indicates a carbon dioxide concentration in the breathing gas, and by a control signal then being selected as a function of the carbon dioxide concentration in the breathing gas for influencing an extent at which the carbon dioxide content passes over from the bloodstream in the device into the gas-flowing area. Hence, a consideration of the actual carbon dioxide concentration in the breathing gas thus takes place when the device for extracorporeal blood gas exchange is controlled.

It may possibly be achieved by the automated method, which is proposed according to the present invention, that a clinician does not himself have to adapt the operating state of the device for extracorporeal blood gas exchange, but that the breathing gas information that indicates the carbon dioxide concentration in the breathing gas is taken into consideration in an automated manner.

It can hereby be achieved that a weaning from the extracorporeal removal of carbon dioxide from the bloodstream is performed by carrying out the method according to the present invention, so that a state, in which an assistance by the ventilator or anesthesia device is only still necessary for the patient, may possibly be achieved at the end of the process; however, the extracorporeal blood gas exchange may possibly be ended.

Known from the state of the art are methods, in which a pump of a device for extracorporeal blood gas exchange is controlled as a function of an EKG signal, as is known from DE 10 2013 012 433 A1 (corresponding U.S. patent application 2015030502 is hereby incorporated by reference in its entirety).

The ventilation of the patient by a ventilator or anesthesia device may preferably be a noninvasive ventilation, so that a ventilation mask is used rather than a tube.

The ventilation of the patient by ventilator or anesthesia device may in this case be a mandatory or else an assisted ventilation.

Thus, a method is provided for controlling a device for extracorporeal blood gas exchange, wherein the device has a membrane as a gas-liquid barrier between a bloodstream and a gas stream, wherein the membrane further makes possible a passing over of the carbon dioxide content from the bloodstream into the gas stream, wherein the device has at least one actuator and wherein a change in a value of an operating parameter of the actuator brings about a change in a value of the carbon dioxide content, which passes over from the bloodstream into the gas stream. The method further comprises: Provision of breathing gas information, which indicates a carbon dioxide concentration in a breathing gas, provision of a control signal which indicates a request for setting a value of the operating parameter, as well as changing of the value of the operating parameter as a function of the carbon dioxide concentration in the breathing gas.

The actuator is preferably a pump for delivering the bloodstream, wherein the operating parameter has an effect on a pumping capacity of the pump of the device for extracorporeal blood gas exchange.

This embodiment is advantageous when the device for extracorporeal blood gas exchange has a pump, which influences at which flow rate the bloodstream flows along the membrane. The pump is thus the actuator of the device in this preferred embodiment. If the pump increases the flow rate of the bloodstream along the membrane, then more carbon dioxide per unit of time is removed from the blood. If the pumping capacity of the pump is lowered, then the flow rate of the bloodstream along the membrane is reduced, so that less carbon dioxide is removed from the bloodstream per unit of time. Hence, the extent at which the carbon dioxide content passes over from the bloodstream into the gas stream can thus be changed by such an operating parameter, which influences a pumping capacity of a pump. In this connection, the operating parameter may be, for example, an actuating current or an actuating voltage of the pump.

The operating parameter preferably influences a quantity of oxygen of the gas stream. In this case, the actuator is preferably simply an oxygen source, wherein the operating parameter influences how much oxygen is fed to the gas stream per unit of time.

The actuator in the form of the oxygen source may especially be configured in this case in the form that a device component of the oxygen source is a valve, which is set in its valve position as a function of the predefined operating parameter value. The operating parameter may then thus be a set value for the valve of the oxygen source. In other words: The operating parameter may be a control position of the valve in this case and a different predefined value for the oxygen source which influences the extent at which oxygen is present in the gas stream.

If, for example, the oxygen quantity, which is available to the membrane per unit of time and thus can pass over into the blood, is increased, then a higher quantity of carbon dioxide must then also pass over from the bloodstream into the gas stream per unit of time because of the equilibrium states of the partial pressures of oxygen and carbon dioxide at the membrane. Hence, due to an influence of the quantity of oxygen of the gas stream, it is thus possible to simply influence at which degree carbon dioxide passes over from the bloodstream into the gas stream.

The method preferably further comprises the steps of the provision of at least one comparison value, which indicates a comparison concentration, as well as the changing of the value of the operating parameter as a function of the carbon dioxide concentration in the breathing gas and as a function of the comparison concentration.

This embodiment is advantageous because by predefining or providing the comparison value, it is possible to check whether or to what extent the passing over of carbon dioxide from the bloodstream into the gas stream is influenced.

In case the carbon dioxide concentration in the breathing gas is higher than the comparison concentration, the value of the at least one operating parameter is preferably changed such that the value of the carbon dioxide content, which passes over from the bloodstream into the gas stream, is reduced.

In case the carbon dioxide concentration in the breathing gas is lower than the comparison concentration, the value of the at least one operating parameter is preferably changed such that the value of the carbon dioxide content, which passes over from the bloodstream into the gas stream, is increased.

These embodiments are advantageous because whenever the carbon dioxide concentration in the breathing gas is above the comparison value, it can be assumed that the gas exchange via the lung is functioning to a certain, sufficient extent. Thus, if the patient succeeds in removing a certain concentration in carbon dioxide from the blood via the breathing gas, then this suggests that his lung capacity has recovered to a certain extent, so that the extent at which carbon dioxide passes over from the bloodstream into the gas stream can be reduced due to a change in the operating parameter. This thus corresponds to the so-called weaning step.

If the carbon dioxide concentration in the breathing gas falls below the comparison value, then it can be assumed that the patient is removing too little carbon dioxide via the lung into the breathing gas, so that the extent at which carbon dioxide passes over from the bloodstream into the gas stream shall be increased due to a change in the operating parameter. Since the patient is thus removing too little carbon dioxide via the lung into the breathing gas, it is thus necessary that more carbon dioxide be removed from the blood within the device for extracorporeal blood gas exchange.

Due to the fact that to determine whether the extent at which carbon dioxide passes over from the bloodstream into the gas stream can be reduced is dependent on a comparison value or on a predefinable comparison concentration, the degree at which the patient is weaned from the extracorporeal blood gas exchange can be fixed by selecting the comparison concentration.

At least one minimal value is preferably provided, wherein in case the at least one operating parameter reaches the minimal value, the value of the at least one operating parameter is retained.

This embodiment is advantageous because by providing or predefining the minimal value, it is possible to determine up to what extent a weaning is performed, so that when the operating parameter has reached the minimal value, the weaning is not carried out further by the method according to the present invention, namely by the operating parameter being retained or left unchanged in its value.

Preferably, an output signal for outputting an optical and/or acoustic warning or information for a clinician can then be outputted when the value of the operating parameter reaches the minimal value. As a result, the clinician is then informed about the fact that a certain degree of weaning is present because of the value of the operating parameter reaching the minimal value.

At least one piece of information is preferably provided, which indicates an extent of a ventilating state of the lung, wherein further a ventilation threshold value is provided and wherein the retaining of the value of the at least one operating parameter is further made dependent on a comparison of the extent of the ventilating state with the ventilation threshold value.

This embodiment is advantageous because, for example, information, which indicates an extent for the ventilating state of the lung of the patient can be provided by a so-called EIT (electrical impedance tomography) device in order to conclusively determine whether the lung capacity of the patient is actually sufficient to be able to perform a removal of carbon dioxide from the bloodstream by means of the lung function only by using a ventilator or anesthesia device without the assistance of a device for extracorporeal blood gas exchange.

Information is preferably provided, which indicates an extent for an inspiratory muscle activity, wherein further an activity threshold value is provided and wherein the retaining of the value of the at least one operating parameter is further made dependent on a comparison of the extent for the inspiratory muscle activity and the activity threshold value.

This embodiment of the present invention is advantageous because, for example, a device for detecting inspiratory muscle activity signals can preferably a signal via sensor signals of electromyography (EMG) sensors. Such a signal is then information correlating to how high an inspiratory muscle activity of the patient is, which can provide information about his own lung capacity. Due to the fact that the value of the operating parameter is finally retained only if the inspiratory muscle activity exceeds a certain activity or the activity threshold value, and also the patient's own inspiratory muscle activity can be taken into account for the final assessment via the patient's own or independent lung capacity.

A first blood gas measured value is preferably provided, which corresponds to a first measurement time, as well as a second blood gas measured value, which corresponds to a second measurement time. An output signal is then provided as a function of the first blood gas measured value and of the second blood gas measured value.

This embodiment is advantageous because blood gas measured values from measurements performed at different times can provide information about whether the patient can independently carry out a sufficient blood gas exchange via his own lungs or airways or else whether an extracorporeal blood gas exchange by means of a corresponding device is still additionally necessary. By taking into account the blood gas measured values of different measurement times, information can then be outputted to the clinician by providing the output signal, so that this clinician can then in turn decide whether or not a weaning of the patient from the treatment by the device for extracorporeal blood gas exchange was successful.

According to a further aspect of the invention a device for extracorporeal blood gas exchange is provide comprising a bloodstream area for guiding a bloodstream, a gas-guiding area for guiding a gas stream, a membrane which forms a gas-liquid barrier between the bloodstream and the gas stream, and which further makes possible a passing over of the carbon dioxide content from the bloodstream into the gas stream, a data network interface, at least one control unit as well as at least one actuator. A change in a value of an operating parameter of the actuator brings about a change in a value of the carbon dioxide content, which passes over from the bloodstream into the gas stream. The control unit is configured to receive a control signal by means of the data network interface, which control signal indicates a request for setting a value of the operating parameter, as well as further to provide the control signal to the actuator.

This device is advantageous because it is hereby possible to be able to control the device via the data network by means of a control signal, in order to influence to what extent the carbon dioxide content passes over from the bloodstream into the gas stream.

According to a further aspect of the invention a device is provided for extracorporeal blood gas exchange, having a bloodstream area for guiding a bloodstream, a gas-guiding area for guiding a gas stream, a membrane which forms a gas-liquid barrier between the bloodstream and the gas stream, and which further makes possible a passing over of the carbon dioxide content of the bloodstream into the gas stream, a data network interface, at least one control unit as well as at least one actuator. A change in a value of an operating parameter of the actuator brings about a change in a value of the carbon dioxide content, which passes over from the bloodstream into the gas stream. The control unit is configured to receive breathing gas information by means of the data network interface, which information indicates a carbon dioxide concentration in a breathing gas, as well as further to provide a control signal, which indicates a request for setting a value of the operating parameter, to the actuator. The control unit is further configured to change the value of the operating parameter as a function of the carbon dioxide concentration in the breathing gas.

This embodiment is advantageous because the device for extracorporeal blood gas exchange can independently set at what extent carbon dioxide passes over from the bloodstream into the gas stream by taking into account the breathing gas information, which indicates the carbon dioxide concentration in the breathing gas.

According to a further aspect of the invention a control device for controlling a device for extracorporeal blood gas exchange is provided. The device for extracorporeal blood gas exchange has a membrane as a gas-liquid barrier between a bloodstream and a gas stream, wherein the membrane further makes possible a passing over of the carbon dioxide content from the bloodstream into the gas stream. The device has at least one actuator. A change in a value of an operating parameter of the actuator brings about a change in a value of the carbon dioxide content, which passes over from the bloodstream into the gas stream. The control device comprises a fluid inlet for receiving a breathing gas, a measuring unit for determining breathing gas information, which indicates a control unit for providing a control signal, which indicates a request for setting a value of the operating parameter. The control unit is configured to select/generate the control signal as a function of the carbon dioxide concentration in the breathing gas.

This embodiment is advantageous because such a device, which can measure a carbon dioxide concentration in the breathing gas via a measuring unit, can independently determine a control signal, in order to then control a device for extracorporeal blood gas exchange with respect to an extent at which carbon dioxide passes over from a bloodstream into a gas stream.

Such a control device is preferably a ventilator or an anesthesia device. Such a control device is preferably a so-called patient monitor or a so-called capnometer.

The control device further preferably has a data network interface, wherein the control unit of the control device is configured to provide the control signal in the form of a data signal of the data network interface.

This embodiment is advantageous because such a control device, which itself has a measuring unit for measuring a carbon dioxide concentration in a breathing gas, can generate or provide a corresponding control signal, as described above, in order to be able to then control the device for extracorporeal blood gas exchange via the data network interface through a data network with respect to an extent at which carbon dioxide passes over from the bloodstream into the gas stream.

According to a further aspect of the invention a control device for controlling a device for extracorporeal blood gas exchange is provided. The device for extracorporeal blood gas exchange has a membrane as a gas-liquid barrier between a bloodstream and a gas stream, wherein the membrane further makes possible a passing over of the carbon dioxide content from the bloodstream into the gas stream, wherein the device has at least one actuator and wherein a change in a value of an operating parameter of the actuator brings about a change in a mass of the carbon dioxide content, which passes over from the bloodstream into the gas stream. The control device comprises a data network interface, which is configured to receive a data signal, which indicates a carbon dioxide concentration in a breathing gas, at least one control unit for providing a control signal, which indicates a request for setting a value of the operating parameter. The control unit is configured to select/generate the control signal as a function of the carbon dioxide concentration in the breathing gas as well as further to provide the control signal in the form of a data signal to the data network interface.

This embodiment of a control device is especially advantageous because it is possible in a data network that such a control device is located at a central location and receives a corresponding data signal, which indicates a carbon dioxide concentration in a breathing gas, in order to then be able to control a device for extracorporeal blood gas exchange with respect to an extent at which carbon dioxide passes over from a bloodstream into a gas stream, via a data signal through a data network. In particular, such a configuration of a control device is advantageous because in a data network such a control device possibly has more computing capacity and/or memory capacity than this is the case, for example, in a device for extracorporeal blood gas exchange or else in a ventilator or anesthesia device or patient monitor. Hence, such a control task can be transferred from a ventilator or anesthesia device or else patient monitor to such a central control device in a data network, so that the device for extracorporeal blood gas exchange also does not have to perform all method steps itself, but rather can be controlled by the central control device of the data network.

The control device is preferably configured by a computer network in a data network or in a so-called cloud.

Advantageous embodiments of the present invention are the subject of the dependent claims and are explained in detail in the following description with partial reference to the figures.

The present invention will be explained in more detail below on the basis of special embodiments without limitation of the general inventive idea on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
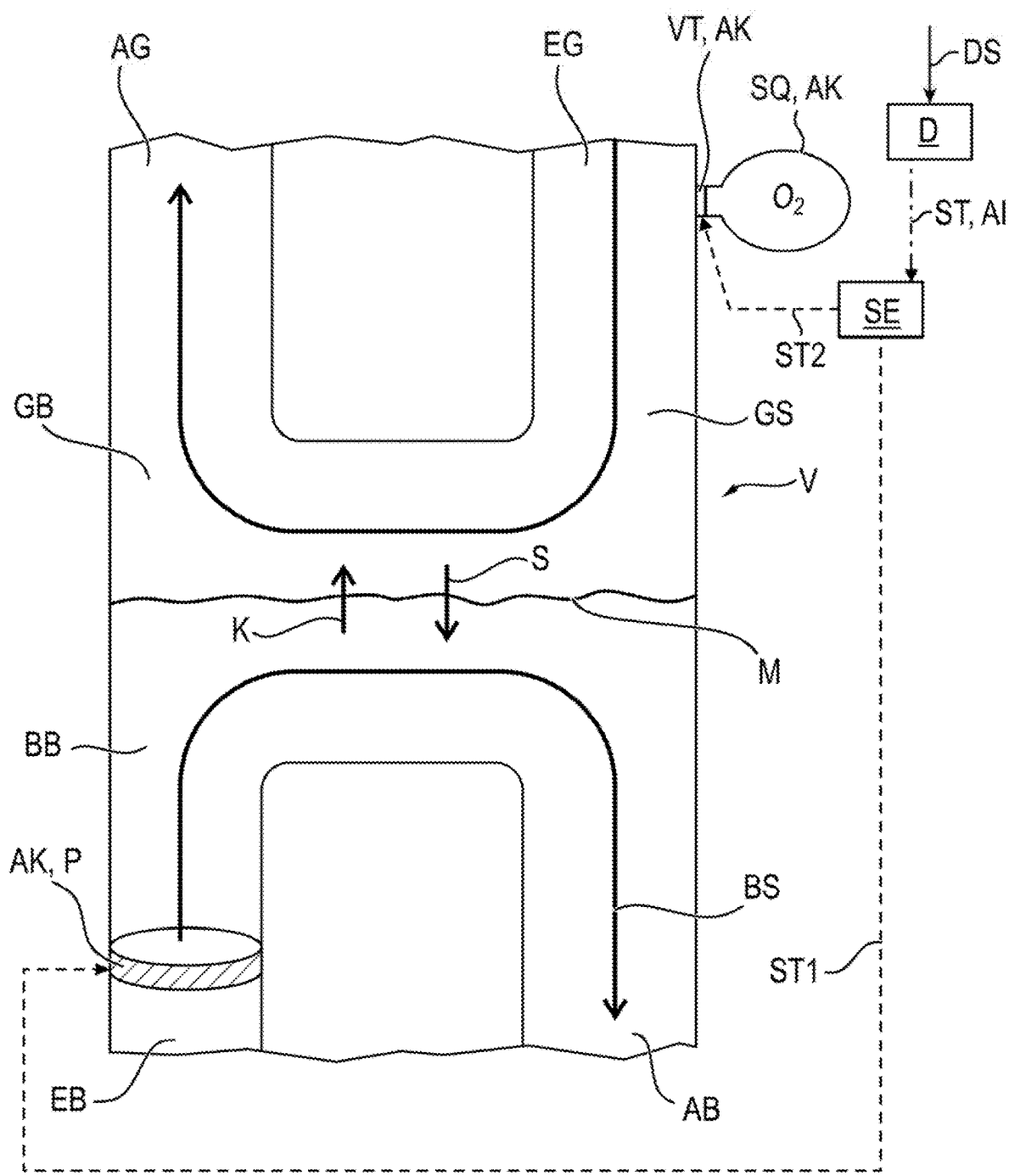
FIG. 1 is a schematic view of a preferred embodiment of a device for extracorporeal blood gas exchange.

Referring to the drawings, the present invention being described herein takes up the following considerations: a standard range for an end-tidal carbon dioxide concentration ($etCO_2$) in a breathing gas of a healthy patient is about 5 vol. % (4.5-6 vol. %). Converted into units of pressure at 1,013 hPa, this results in ~35-45 mmHG as $CO_2$ partial pressure. The ambient air pressure (1 vol. %=7 mmHG; 1 mmHG=0.15 vol. %; 1 mmHG=1.333 hPa) is included in such a conversion. The carbon dioxide partial pressure in the end-tidal exhaled gas ($etCO_2$) is about 3-5 mmHG lower than the arterial $CO_2$ partial pressure of ~45 mmHG in the blood ($paCO_2$). The alveolar $CO_2$ partial pressure ($pACO_2$) is between the $paCO_2$ and $etCO_2$. In case of rebreathing of exhaled breathing gas or due to "shallow breathing" (hypoventilation), the $etCO_2$ concentration in the breathing gas increases. When less $CO_2$ can be exhaled due to hyperventilation or lung diseases, e.g., obstruction or COPD, the $etCO_2$ concentration in the breathing gas drops.

This means that after a reduction in removal of carbon dioxide from the blood by means of a device for extracorporeal blood gas exchange from a previously stable overall situation, the carbon dioxide concentration in the breathing gas drops, if the lung or the lung capacity of the patient has not yet recovered sufficiently. If this is the case, the removal of carbon dioxide from the blood by the device for extracorporeal blood gas exchange must be increased again.

In case the carbon dioxide concentration in the breathing gas does not change considerably after a reduction in the removal of carbon dioxide from the blood by the device for extracorporeal blood gas exchange from a previously stable overall situation, then it can be inferred that the lung or the lung capacity of the patient has recovered to a certain extent, so that the reduction in the removal of carbon dioxide from the blood by the device for extracorporeal blood gas exchange can be retained.

FIG. 1 shows a device V for extracorporeal blood gas exchange. A bloodstream BS is guided via a blood inlet EB along a membrane M and then removed again via a blood outlet AB. The device V preferably has an actuator AK in the form of a pump P, which influences the flow rate of the bloodstream BS along the membrane M.

The bloodstream is thus guided in a bloodstream area BB along the membrane M.

The membrane M separates the bloodstream BS or the bloodstream area BB from a gas stream GS or a gas-guiding area GB.

The gas stream GS is guided from a gas inlet EG along the membrane M to a gas outlet GA.

A quantity of oxygen which is fed to the gas stream GS is controlled via an oxygen source SQ. The oxygen source SQ can preferably be regarded as an actuator AK. The oxygen source SQ has a device component as actuator AK in the form of a valve VT in order to influence the quantity of oxygen of the gas stream GS.

A control unit SE preferably provides a control signal ST1 to the pump P as actuator AK in order to influence the pumping capacity of the pump P.

The control unit SE preferably provides a control signal ST2 to the oxygen source SQ or to the valve VT in order to influence the quantity of oxygen to the gas stream GS.

A certain carbon dioxide content K passes over from the bloodstream BS into the gas stream GS at the membrane. Likewise, oxygen S passes over from the gas stream GS into the bloodstream BS to a certain extent.

If the flow rate of the bloodstream BS is increased by a change in the pumping capacity of the pump P, then the extent at which the carbon dioxide content K passes over from the bloodstream BS into the gas stream GS per unit of time is also increased.

If the oxygen quantity of the gas stream GS is increased, then the extent at which oxygen S passes over from the gas stream GS into the bloodstream BS per unit of time is also increased, wherein the extent at which carbon dioxide K passes over from the bloodstream through the membrane into the gas stream GS is then also increased because of the equilibrium states of the oxygen and carbon dioxide partial pressures at the membrane.

Thus, it is possible to influence at what extent carbon dioxide K passes over from the bloodstream BS into the gas stream GS on the one hand, due to an action of the control unit SE on the oxygen source SQ or on the valve VT by means of the control signal ST2 as well as, on the other hand, due to an action of the control unit SE on the pump P by means of the control signal ST1.

The device V further has a data interface D, via which the data interface D can receive one or more data signals DS.

In a first preferred embodiment, a control signal ST is received by means of the data signal DS at the data network interface D, wherein the control signal ST indicates a request to set a value of an operating parameter of an actuator AK. A change in a value of such an operating parameter brings about a change in the value of the carbon dioxide content K which passes over from the bloodstream BS into the gas stream GS.

In a first preferred embodiment, the control unit SE is configured to provide the control signal ST at one or more of the actuators AK, SQ, VT, P. In case the device V thus preferably has a pump P as actuator AK, the control unit SE selects the control signal ST1 on the basis of the control signal ST received via the data network interface D. Likewise, the control unit SE preferably selects the control signal ST2 to control the valve VT or the oxygen source SQ on the basis of the control signal ST.

As a result, it is thus made possible that the device V for extracorporeal blood gas exchange can be checked or controlled via the data network interface D with respect to the extent at which carbon dioxide passes over from the bloodstream BS into the gas stream GS.

According to a preferred embodiment, the device V receives breathing gas information AI in the form of the data signal DS via the data network interface D, wherein the breathing gas information AI indicates a carbon dioxide concentration in a breathing gas. The control unit SE then provides a control signal ST1 and/or ST2 to at least one actuator AK, wherein the control unit SE selects the value of the operating parameter, which is requested in the control signal, as a function of the carbon dioxide concentration, which is indicated in the breathing gas information AI.

It is consequently possible, on the one hand, that the device V is controlled via the data network interface D by means of receiving the signal ST in the form of the data signal DS by a different unit in the data network. As an alternative, it is possible that the device V receives the breathing gas information AI, which indicates the carbon dioxide concentration in the breathing gas, and then itself selects the corresponding control signals ST1, ST2 as a function of this indicated carbon dioxide concentration in the breathing gas.

Figure 5A:
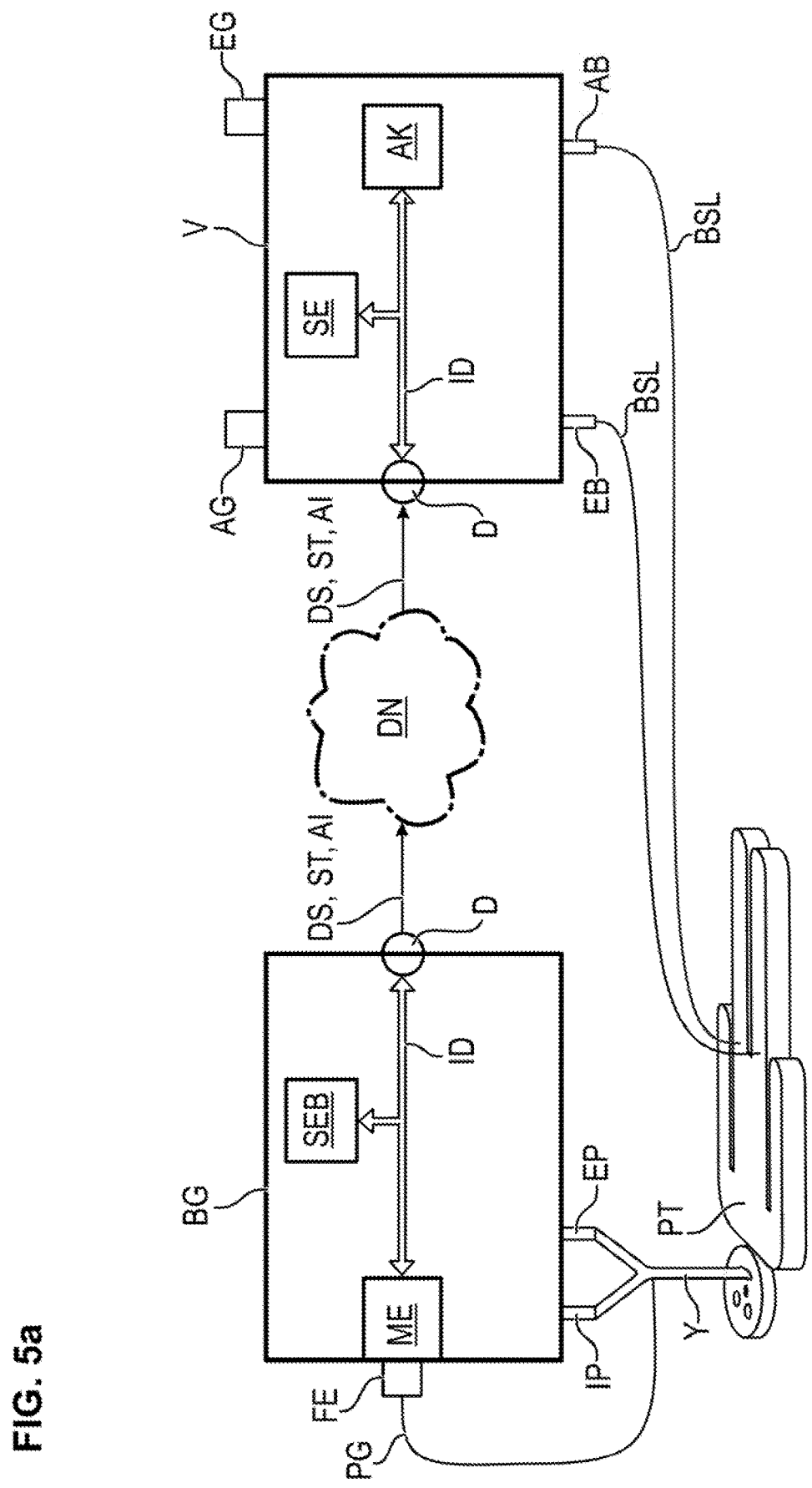
FIG. 5a is a schematic view showing an interaction of the device for extracorporeal blood gas exchange according to the present invention with an embodiment of a control device for controlling the device for extracorporeal blood gas exchange.
Figure 5B:
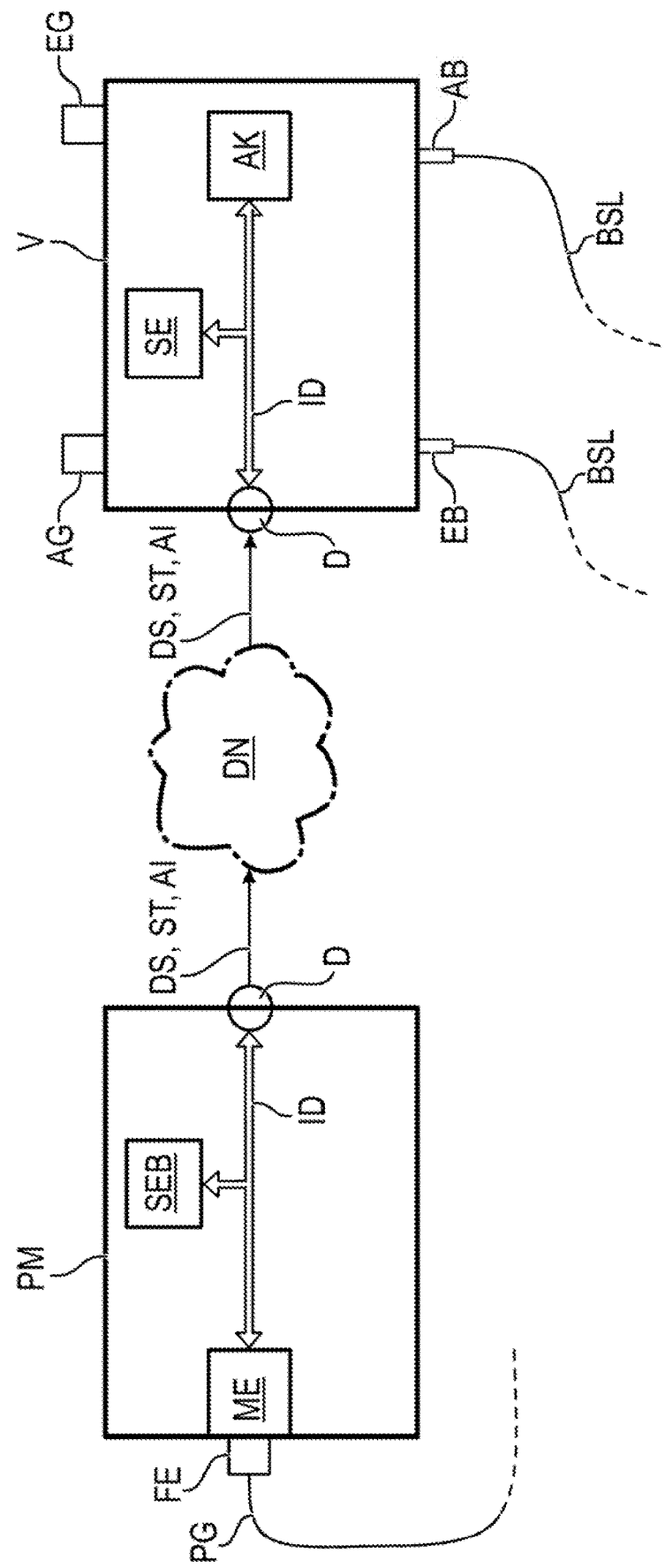
FIG. 5b is a schematic view showing an interaction of the device for extracorporeal blood gas exchange according to the present invention with another embodiment of a control device for controlling the device for extracorporeal blood gas exchange.

For this, preferred interactions or preferred forms of interaction of a device for extracorporeal blood gas exchange with corresponding control devices are shown in FIGS. 5a and 5b.

According to FIG. 5a, the patient PT is ventilated by a ventilator or anesthesia device BG via a ventilation tube, which leads to the patient PT by means of a Y-piece Y via an inspiratory port IP and an expiratory port EP. A sample gas line PG, which picks up a sample gas quantity at the Y-piece Y, leads to a fluid inlet FE of the ventilator or anesthesia device BG.

The patient is further connected to the device V for extracorporeal blood gas exchange via bloodstream lines BSL as explained above by means of venous and/or arterial accesses.

A measuring unit ME is configured to determine a carbon dioxide concentration in the breathing gas by analyzing the gas sample from the sample gas line PG. The device BG further has a control unit SEB as well as preferably a data network interface D for the exchange of data signals DS. The measuring unit ME, the control unit SEB as well as the data network interface D are preferably connected to one another via an internal data bus ID.

The ventilator or anesthesia device BG may in this case be configured as a control device to control a device V for extracorporeal blood gas exchange. The control unit SEB of the ventilator BG may hereby provide a corresponding control signal ST in the form of a data signal DS to the device V.

The device V may then use the data signal DS or control signal ST received via the data interface D by means of its control unit SE in order to actuate an actuator AK correspondingly. The data interface D, the control unit SE as well as the actuator AK are preferably connected to one another by an internal data bus ID.

In case the ventilator BG itself is the control device for controlling the device V for extracorporeal blood gas exchange, the control unit SEB provides the control signal ST as a function of the carbon dioxide concentration in the breathing gas measured by the measuring unit ME. In case the device for extracorporeal blood gas exchange V itself performs the control, the measuring unit ME measures a carbon dioxide concentration in the breathing gas and the device BG transmits breathing gas information AI in the form of a data signal DS to the device V. These two cases correspond to the explanations in reference to FIG. 1 with respect to the control signal ST and the breathing gas information AI.

FIG. 5b shows an alternative embodiment of a control device for controlling a device V for extracorporeal blood gas exchange in the form of a so-called patient monitor PM. The patient monitor PM may, as an alternative, be a so-called capnometer. In this case, the patient monitor PM differs from the ventilator or anesthesia device BG from FIG. 5a in that the patient monitor PM itself does not perform the ventilation of the patient PT from FIG. 5a. However, the patient monitor PM has a fluid inlet FE for connection to a sample gas line PG. By means of a measuring unit ME, the patient monitor PM then measures the carbon dioxide concentration in the breathing gas, which is brought to the fluid inlet via the sample gas line.

The patient monitor PM as a control device for controlling a device V for extracorporeal blood gas exchange may then select a control signal ST and provide it in the form of a data signal DS, as explained above in reference to FIG. 5a with respect to the ventilator or anesthesia device BG. In case the device for extracorporeal blood gas exchange V itself performs the control, the measuring unit ME measures a carbon dioxide concentration in the breathing gas and the patient monitor PM transmits breathing gas information AI in the form of a data signal DS to the device V. These two cases correspond to the explanations in reference to FIG. 1 with respect to the control signal ST and the breathing gas information AI.

Figure 6:
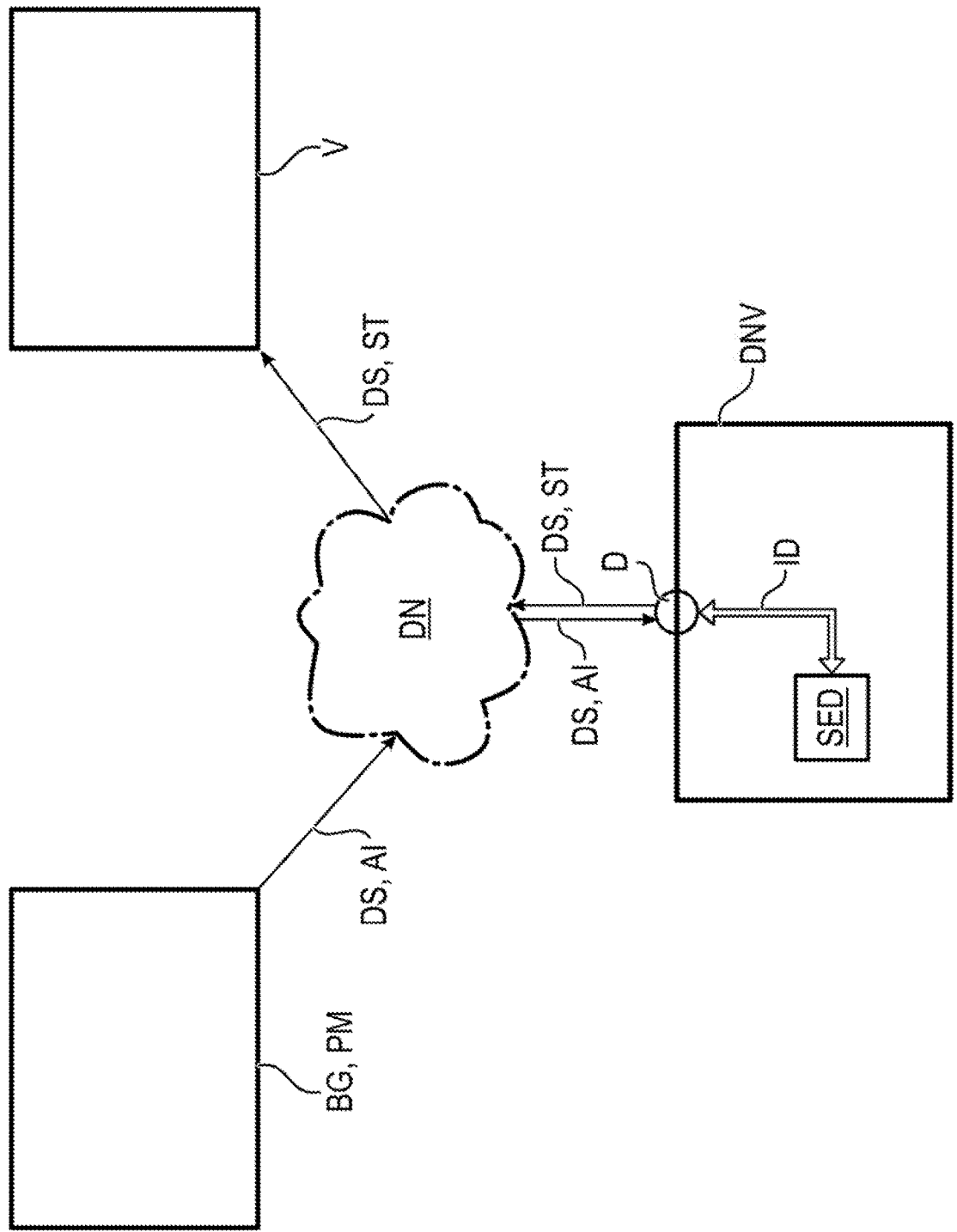
FIG. 6 is a schematic view showing a preferred embodiment of a control device for controlling a device for extracorporeal blood gas exchange over a data network.

FIG. 6 shows another preferred embodiment of a control device DNV for controlling the device V for extracorporeal blood gas exchange.

The control device DNV has a data network interface D, via which the control device DNV exchanges data signals DS via a data network DN with the device V for extracorporeal blood gas exchange as well as a device BG, PM for providing breathing gas information, which indicates a carbon dioxide concentration in a breathing gas.

The control device DNV may thus receive via the data network interface D a data signal DS, which indicates a carbon dioxide concentration in a breathing gas. Such a data signal DS or such breathing gas information may be provided, for example, by a ventilator or anesthesia device BG or by a patient monitor PM, which were described above in reference to FIGS. 5a and 5b, and may be transmitted in the form of data signals DS to the control device DNV.

The control device DNV has a control unit SED, which provides a control signal ST in the form of a data signal DS to the data network interface. Such a data signal DS may then contain or indicate a corresponding control signal ST.

The control unit SED then selects the control signal ST as a function of the indicated carbon dioxide concentration in the breathing gas.

Figure 2:
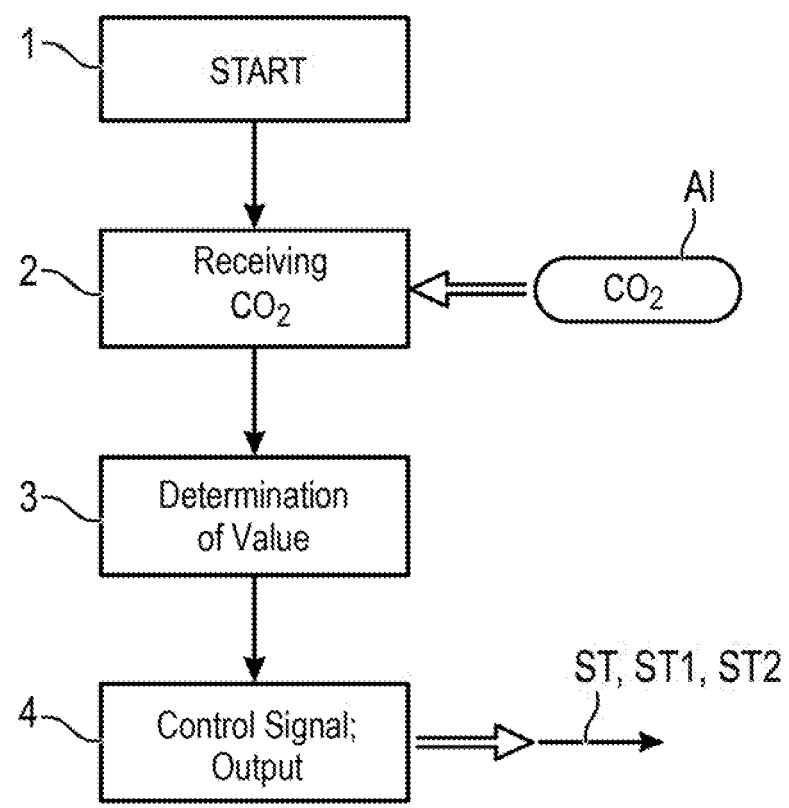
FIG. 2 is a flow chart of steps of the method according to the present invention.

FIG. 2 shows the steps of the method according to the present invention. The method according to the present invention may preferably be carried out on the device V according to the present invention of FIG. 1. The method according to the present invention of FIG. 2 may preferably be implemented by a control device BG, PM, DNV of FIGS. 5a, 5b or FIG. 6 carrying out the method according to the present invention.

The method according to the present invention begins in a start situation of a step 1. Breathing gas information AI, which indicates a carbon dioxide concentration in a breathing gas, is provided in a step 2. In the example of the device V of FIG. 1, this takes place via a corresponding data signal DS. This takes place as an internal providing of a measured value of the corresponding measuring unit ME to the corresponding control unit SEB in the example of the devices BG, PM as control device of FIGS. 5a as well as 5b. In the example of the device DNV as control device, this takes place via a corresponding data signal DS.

A value for an operating parameter is determined in a step 3, wherein this takes place as a function of the carbon dioxide concentration in the breathing gas.

A control signal ST is outputted in a step 4. In the example of the device V of FIG. 1, this is an output of a control signal ST1 and/or ST2 to one or more actuators AK. In the example of the control devices BG, PM of FIG. 5a as well as 5b, this may take place in the form of data signals DS, which have or indicate the corresponding control signal ST. In the example of FIG. 6, the control device DNV may provide the control signal ST as a data signal DS to the device V.

Figure 3:
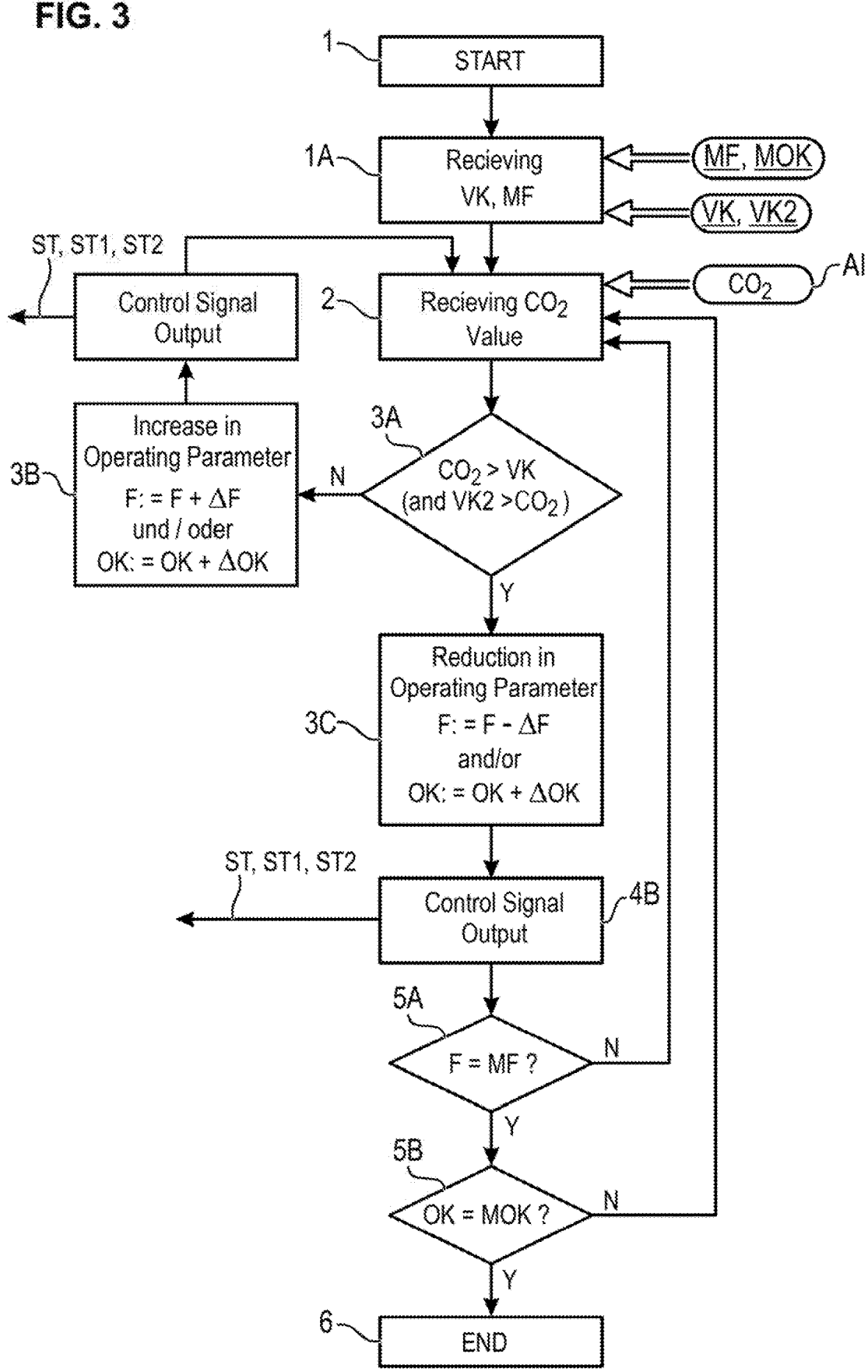
FIG. 3 is a flow chart of a preferred embodiment of the method according to the present invention.

FIG. 3 shows a preferred embodiment of the method according to the present invention.

After the starting step 1, a provided minimal value MF is preferably received in a next step 1A. A plurality of minimal values MF, MOK, which refer to corresponding operating parameters, are preferably provided.

Further, a provided comparison concentration or a comparison value VK is provided or received.

The provided breathing gas information AI is then received in step 2.

A comparison of the carbon dioxide concentration with the comparison value VK is carried out in step 3A. A change in values of the operating parameter is then carried out as a function of a result of this comparison.

If the carbon dioxide concentration is above the comparison value VK, then the process is branched off to a step 3C, in which a value of the operating parameter is changed such that the value of the carbon dioxide content, which passes over from the bloodstream into the gas stream, is reduced. A flow rate F, which can be performed by a pump P of FIG. 1, is preferably reduced by a predefined threshold value F. In addition or as an alternative, an oxygen quantity OK, which is guided to the gas stream GS of FIG. 1, is reduced by the threshold value OK.

The above-mentioned control signal, which may be one of the control signals ST, ST1, ST2, is then outputted in a step 4B.

It is then checked in a step 5A whether the value F of the operating parameter has reached the minimal value MF. If this is not the case, then the process is branched off back to step 2.

If this is the case, then step 5B can preferably be carried out, which, however, is not mandatory.

The process could, in principle, be branched off from step 5A directly to step 6, which ends the method, so that the value of the operating parameter F is then retained.

The value OK of the operating parameter is preferably checked in step 5B to the effect whether this value has reached a corresponding minimal value MOK.

Only if this is the case, the process is actually branched off to step 6, in which the operating parameter is then also left unchanged or the operating parameters are left unchanged.

If it should be determined in step 5B that the corresponding operating parameter OK has not yet reached the corresponding minimal value MOK, then the process is branched off back to step 2.

An embodiment of the method outlined here may be that only the operating parameter F as an influence of the pumping capacity of the pump P of FIG. 1 is changed. In this case, the operating parameter may preferably be left unchanged in relation to the oxygen content of the gas stream. This may then be the case if the device V has a pump P.

In case of a so-called pECLA device, only the quantity of oxygen OK is preferably changed as an operating parameter, because then no pump P of the device V of FIG. 1 is present as actuator AK.

If it was determined in step 3A that the carbon dioxide concentration is above the comparison value VK, then the process can be branched off to a step 3B, in which one or both of the operating parameters F, OK as pumping capacity of the pump or as oxygen quantity of the gas stream are changed such that the extent at which carbon dioxide passes over from the bloodstream into the gas stream, is increased. This preferably takes place only if the carbon dioxide concentration is below another comparison value VK2.

A step 4A, in which a corresponding control signal ST, ST1, ST2 is outputted, takes place in turn in step 3B.

The process is then branched off back to step 2 of the method.

It is possible that in step 2 the breathing gas information AI is a so-called end-tidal carbon dioxide concentration. Such a carbon dioxide concentration is then preferably averaged over time in step 2, so that step 2 lasts a certain period of time.

The breathing gas information AI is preferably already a carbon dioxide concentration measured value averaged over time.

It is not necessary that the carbon dioxide concentration be absolutely an end-tidal concentration. Other carbon dioxide concentrations of a breathing gas are also conceivable.

Figure 4:
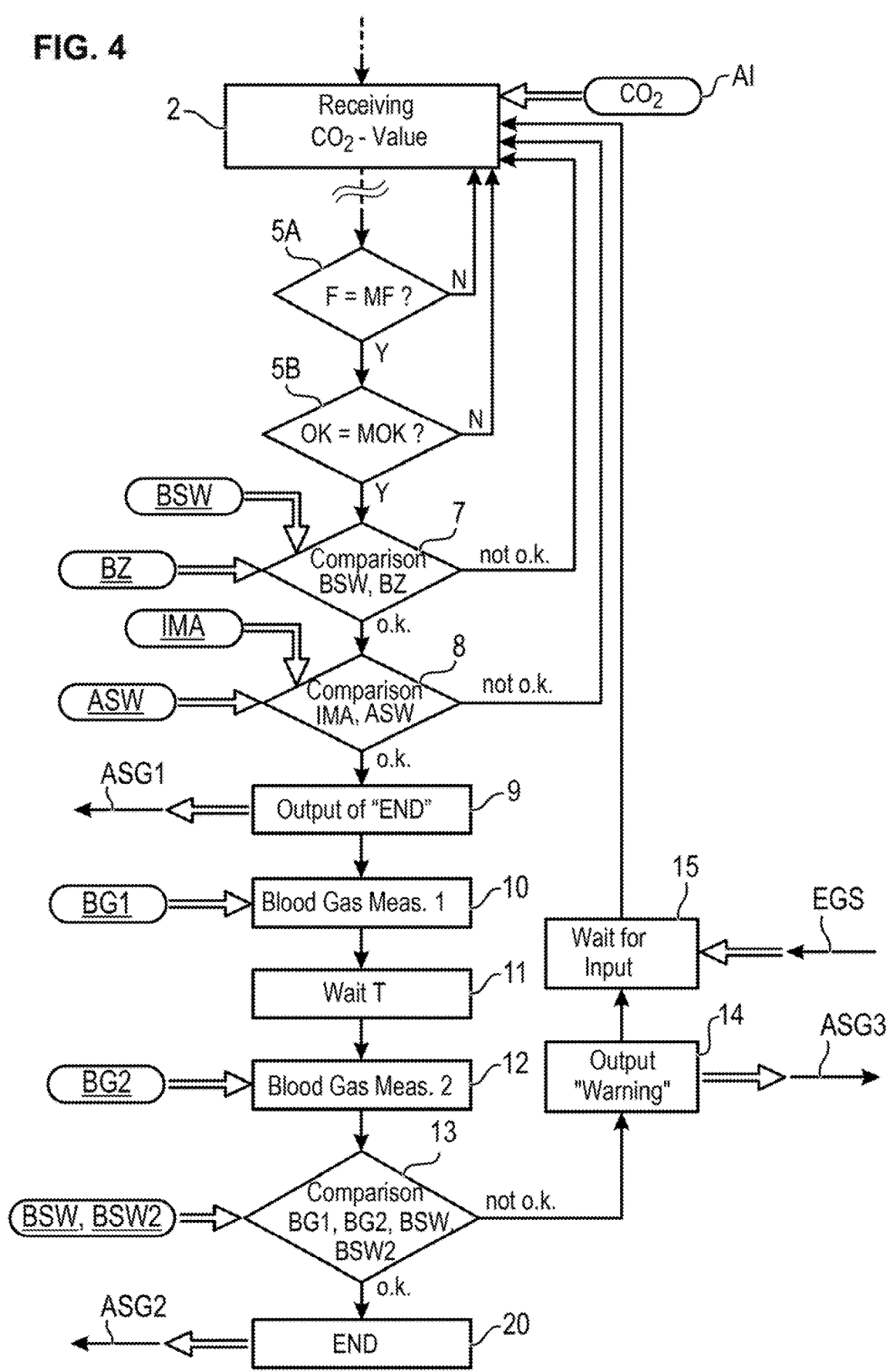
FIG. 4 is a flow chart of possible additional steps for carrying out the method according to the present invention in a preferred embodiment.

FIG. 4 shows other steps preferably to be carried out according to a preferred embodiment of the method according to the present invention.

From the steps of the embodiment of the method of FIG. 3, first step 2 is once again shown here, in which the breathing gas information AI is received.

Other steps, which replace step 6 of FIG. 3, then follow the later following step 5A as well as step 5B, which preferably takes place.

A ventilation threshold value BESW as well as at least one piece of information BZ, which indicates an extent for a ventilating state of a lung, are provided and received in a step 7. Such information, which indicates an extent for a ventilating state, may be provided by an electrical impedance tomography (EIT) device. A comparison of the extent for the ventilating state and the ventilation threshold value is then carried out. Whether the value of the at least one operating parameter is retained is made dependent on this. If it appears by this comparison that the ventilating state of the lung is fine, then the process is branched off further downwards, so that the method for changing the value of the operating parameter as a function of the carbon dioxide concentration is finally ended in step 9.

If the comparison of the result is that the ventilating state of the lung is not fine, then the process is branched off back to step 2.

An indicator of a ventilating state of a lung may be the so-called index value RVD as an indicator of a ventilation of the lung. The RVD index is an indicator of regional ventilation delays, as is also known from the documents DE 10 2015 006 902 B3 (corresponding U.S. publication US 2016/0354007 is hereby incorporated by reference in its entirety), or 'Thomas Muders et al. "Tidal recruitment assessed by electrical impedance tomography and computed tomography in a porcine model of lung injury".'

According to the Muders study, the RVD index quantifies a delay time of individual lung regions during inhalation, which delay time is standardized to a global inflow period. An impedance value of 40% of the maximum amplitude in the respective—global or regional—course of the impedance curve over the entire duration of inhalation is always selected here as amplitude criterion. RVD values, which can be represented as an RVD map, are then obtained for a plurality of lung regions. An inhomogeneity of the ventilation of lung regions can then be assessed by means of averaging and standard deviation of the RVD values over all individual lung regions. A high regional RVD index is characteristic of pronounced disturbances in the ventilation of the regions of the lung, i.e., a high averaged RVD index characterizes a nonuniform lung ventilation.

Since EIT does not detect absolute impedance changes but rather relative impedance changes and makes an assessment for representing the ventilation situation, there is no uniform standard range for the RVD index. In addition, a 10% threshold value is used instead of the above-mentioned 40% threshold value of the impedance curve in other studies. The following relative RVD criterion, for example, may be applied as an indicator of "recovery" of the lung during the weaning: The RVD index has increased by less than 5-10% after the weaning step has been carried out since the last EIT data collection.

The information BZ is thus preferably information, which indicates measured values RVD1 or RVD2 of different times. In case a percentage change in the measured values falls below the ventilation threshold value BESW, it can be inferred that the ventilating state of the lung is fine $$|RVD1-RVD2|/RVD2 < BESW$$

with preferably BESW from a value range of 5% to 10%.

Another indicator of a ventilating state of a lung—or other measured values—may be an indicator of a ratio of ventilation and perfusion V/Q. Such an indicator is known from the documents DE 102014009439 A1 (corresponding U.S. Pat. No. 9,384,549 is hereby incorporated by reference) or EP 1292224 (corresponding U.S. Pat. No. 7,435,226 is hereby incorporated by reference).

A blood exchange in the lung of 5 L/min and a breathing gas exchange of 4 L/min, i.e., a V/Q value of 0.8, are obtained for an average healthy person.

Assuming that the ventilation remains unchanged at the ventilator, a relative V/Q criterion may be applied as an indicator of "recovery" of the lung during the weaning Both an improvement in the perfusion and an improvement in the ventilation are expected as the effects of recovery.

Depending on the clinical picture, a patient with reduced perfusion or with reduced ventilation may be present, which can be detected, e.g., on the basis of the V/Q index.

When the V/Q index has changed by less than +5% for consecutive measurement times, it can then be inferred that the comparison of the information BZ with the weaning step at least does not cause any negative change.

The information BZ is thus preferably information, which indicates measured values VQ1 and VQ2 of different times. In case a percentage change in the measured values falls below the ventilation threshold value BESW, it can be inferred that the ventilating state of the lung is fine $$|VQ1-VQ2|/VQ2 < BESW$$

with preferably BESW=5%.

Another indicator of a ventilating state in the lung may be an indicator of a lung outer contour. This is also known from the document DE 10 2014 018 107 A1 (corresponding U.S. Publication 2016/0163062 A1 is incorporated herein by reference in its entirety).

An enlargement of the active, maximum lung area in the dorsal view that can be ventilated with the mechanical ventilation of the lung can be used as an indicator of "recovery" of the lung during the weaning. The lung area available for the gas exchange along a horizontal sectional plane is, in this case, to be viewed synonymously for an overall surface of all alveoli. For example, an enlargement of the lung outer contour, especially of the circumference of the lung, can be used as an indicator of the enlargement of the lung area available for the ventilation.

Since the thoracic circumferences of different people and thus the maximum space that the lung can occupy therein are highly individual and different depending on height, age, gender, body weight, there are no standard ranges for thoracic circumferences or maximum lung outer contours.

Thus, the relative change in circumference, for example, as a relative criterion may be used as an indicator of "recovery" of the lung during the weaning:

The circumference of the determined maximum lung outer contour has increased by more than 5-10% after the weaning step has been carried out since the last EIT data collection or the determined circumference has been changed/reduced at least not considerably (e.g., +5%).

The information BZ is thus preferably information which indicates measured values for a lung outer contour LA1 or LA2 at different times. In case a percentage change in the measured values may fall below the ventilation threshold value BESW, it can be inferred that the ventilating state of the lung is fine $$|LA1-LA2|/LA2 < BESW$$

with preferably BESW=5% . . . 10%.

The information BZ as well as the threshold value BESW may be received via a data interface D, for example, the data interface D of the device V of FIG. 1, the data interface D of the device BG of FIG. 5*a*, the data interface D of the device PM of FIG. 5*b* or the data interface D of the device DNV of FIG. 6. Such information BZ is usually provided by an EIT device in the form of a data signal. In case the threshold value BESW is not provided via a data signal DS, the threshold value BESW may also be provided on an internal memory of one of the devices V of FIG. 1, BG of FIG. 6*a*, PM of FIG. 5*b* or DNV of FIG. 6. Such a memory unit is not shown explicitly in the figures here.

Information IMA, which indicates an indicator of an inspiratory muscle activity, is provided and received in a step 8. This is preferably carried out via a data signal, wherein this data signal can be received in a similar manner at various devices, as explained above in reference to the information BZ.

Furthermore, an activity threshold value ASW is provided and received, wherein this provision or receiving may take place in a manner similar to the threshold value BESW.

The retaining of the value of the operating parameter is further made dependent on a comparison of the indicator of the inspiratory muscle activity and the activity threshold ASW to the effect that in case the inspiratory muscle activity is sufficiently high, the process is then branched off to step 9, in which the value of the operating parameter is then retained or left unchanged.

If the comparison of the indicator of the inspiratory muscle activity with the activity threshold value is not satisfactory, the process is then branched off back to step 2 of the method.

An indicator of an inspiratory muscle activity may be provided by an external device, for example, a device for determining muscle activity signals on the basis of sensor signals of electromyographic sensors. Methods for determining signals of inspiratory muscle activity are known from German Patent Application No. 102015015296.3. An indicator of an inspiratory muscle activity may in this case be an energy of such a processed sensor signal, which can then be compared with a minimal value for a signal energy as the activity threshold value. As a result, it can be detected whether the possibility for spontaneous breathing by the patient is already present such that he can sufficiently breathe independently.

Finally, as explained above in reference to FIG. 3 with respect to step 6, the at least one operating parameter is then left unchanged in step 9. In this connection, an output signal ASG1 is preferably outputted as information about the fact that the operating parameter, for example, the pumping capacity of the pump or else the oxygen quantity of the oxygen source, has reached a corresponding minimal value.

A blood gas measured value BG1, which corresponds to a first measurement time, is then received or provided in another step 10.

One then preferably waits in a step 11 for a predefined time T.

A second blood gas measured value BG2, which corresponds to a second measurement time, is received or provided at a later, second time.

A comparison of the blood gas measured values BG1, BG2 is then carried out in a step 13, taking a provided blood gas threshold value BSW into consideration.

For a patient, in whom the removal of carbon dioxide from the blood via his own lung capacity or lung is sufficient, it can then be inferred from values of a blood gas measurement at different times that the patient is maintaining a sufficiently stable condition or that his own lung capacity is sufficient for the removal of carbon dioxide from the blood.

In case an analysis of the blood gas measured value BG1, BG2 as well as the blood threshold value BSW indicates a sufficient recovery of the breathing organs, the process may then be branched off to a step 20, in which the method is finally ended. An output signal ASG2 may then be outputted in step 20, which output signal informs a clinician about the fact that the analysis of the blood gas measured values BG1, BG2 was satisfactory.

Depending on the type of blood gas threshold value, the analysis of the blood gas measured values BG1, BG2 as well as of the blood threshold value BSW is preferably satisfactory if the blood gas measured values BG1, BG2 both fall below the blood threshold value BSW $$BG1, BG2 < BSW.$$

Depending on the type of blood gas measured value, the analysis of the blood gas measured value BG1, BG2 as well as of the blood threshold value BSW may preferably also be satisfactory, however, if the blood gas threshold values BG1, BG2 both exceed the blood threshold value BSW $$BG1, BG2 > BSW.$$

The analysis of the blood gas measured values BG1, BG2 as well as of the blood threshold value BSW2 is preferably satisfactory if, as an alternative or in addition, a difference in quantity in the blood gas measured values BG1, BG2 falls below the other blood threshold value BSW2

$$|BG1-BG2| < BSW2,$$

because then a change in the blood gas value over time is sufficiently minor.

A type of blood gas value may be, for example:
a carbon dioxide partial pressure of the blood $pCO_2$,
an oxygen partial pressure of the blood $pO_2$,
or a pH value of the blood.

A corresponding, individual threshold value BSW and/or BSW2 can then be selected or predefined for a corresponding blood gas value.

The carbon dioxide partial pressure in the blood $pCO_2$ as a type of blood gas measured value is, for example, within a normal range of 40 mmHG, preferably 36 mmHG to 44 mmHG in healthy adults. The carbon dioxide partial pressure in the blood $pCO_2$ is increased when the overall removal of carbon dioxide from the blood by means of breathing and extracorporeal blood gas exchange is not sufficient during weaning A sufficiently recovered breathing of a patient lowers the carbon dioxide partial pressure in the blood. The threshold value BSW related to the carbon dioxide partial pressure in the blood is selected to be, e.g., 44 mmHG, wherein the blood gas values BG1, BG2 have to be lower than the threshold value BSW. The threshold value BSW2 related to the difference in quantity of the carbon dioxide partial pressure measured values in the blood is selected to be, e.g., 1 mmHG to 3 mmHG.

A pH value as a type of blood gas measured value is, e.g., in a standard range for values of 7.35 to 7.45 for adults. If values of 0<7.35 are present, then this is called hyperacidification or acidosis. If values of 7.45 to 14 are present, then this is called hypoacidification or alkalosis. The pH value is especially connected to an increase in the carbon dioxide partial pressure in the blood in case of a respiratory disturbance. Carbon dioxide dissolved in the blood is an acid (carbonic acid), i.e., when the carbon dioxide value in the blood is increased, the pH value is, for example, lower than 7.32. The blood gas values BG1, BG2 have to be lower than a threshold value BSW of, e.g., 7.32. The threshold value BSW2 related to the difference in quantity of the pH measured values in the blood is selected to be, e.g., 0.1 to 0.3.

The oxygen partial pressure $pO_2$ as a type of blood gas measured value is, e.g., in a normal range for values of 75-97 mmHG for adults. The blood gas values BG1, BG2 must be lower than a threshold value BSW of, e.g., 75 mmHG. The threshold value BSW2 related to the difference in quantity of the oxygen partial pressure measured values BG1, BG2 is selected here to be, e.g., 5 mmHG to 7 mmHG.

Further, a base excess (BE) value may be used as a type of blood gas measured value, which base excess value makes it possible to assess the metabolism or the non-breathing-related portions of disturbances of the metabolism in the acid-base balance. It the acid-base balance is assessed in connection with the $pCO_2$ partial pressure in order to confirm a diagnosis of respiratory acidosis, for example. Since the BE value within the framework of a blood gas analysis is often also determined anyway, the BE value can be used in addition to the $pCO_2$ partial pressure in certain situations and in a patient-type-specific manner (e.g., clinical pictures with base loss in case of intensified loss of fluid (diarrhea)) in order to suspend the weaning, for example, in such a situation (diarrhea) or the ending of the weaning with disconnection from the device for extracorporeal blood gas exchange until this situation (diarrhea) has improved.

The output signals ASG1, ASG2 may be output signals for actuating an optical and/or acoustic output unit. Further, the output signals ASG1, ASG2 may be such that these output signals are provided in the form of data signals to data network interfaces at other network units in order to then be used there for an actuation of optical and/or acoustic output units.

If a comparison of the blood gas measured value of the threshold value BSW is not satisfactory, then the process is branched off back to a step 14, in which an output signal ASG3 is outputted, which indicates a warning. This output signal ASG3 may also be provided in a different form, as already explained above in reference to the output signals ASG1, ASG2.

The blood gas values BG1, BG2 are thus taken into consideration such that after completion of the method for changing the value of the operating parameter, it is possible to verify whether a capacity of the lung for gas exchange is present to a sufficient extent, and thus ending of the extracorporeal lung assistance may now be carried out. In this connection, blood gas values may emerge from a blood gas analysis.

A step 15 then follows, in which one waits for an input of an input signal EGS by an input unit. As a result, a clinician is enabled to let the method for changing the value of the operating parameter restart due to the input of the input signal EGS, so that the process is then branched off back to step 2.

According to the proposed method, an operating parameter, for example, a pumping capacity F or oxygen quantity OK, is reduced according to a predefined increment F or OK in an embodiment from FIG. 3. These increments may be selected depending on the patient. This may take place, for example, by a receiving of corresponding increment values via the data interface D in the form of data signals DS, see FIG. 1. Likewise, in case the devices BG of FIG. 5*a*, PM of FIG. 5*b* or DNV of FIG. 6 are the devices carrying out the method, the increment values F, OK may be received as data signals DS. Such values in the form of data signals DS may be predefined, for example, by a central IT system of a clinical setting. As an alternative, it is possible that the device V of FIG. 1, the device BG of FIG. 5*a*, the device PM of FIG. 5*b* or the device DNV of FIG. 6 receive data, for example, age, height, body weight or past medical history as well as current clinical picture as additional information in the form of data signals DS from a patient data management system and then correspondingly selects the increment values F, OK on the basis of these data signals or the content thereof.

The statements made above for the increment values F, OK may also apply to one or more of the following values:
comparison values VK, VK2
minimal values MF, MOK,
ventilation threshold value BESW,
activity threshold value ASW,
blood gas threshold values BSW, BSW2.

Even though some aspects were described in connection with a device or a plurality of devices, it is understood that these aspects also represent a description of the corresponding method, so that a block or a component of a device is also defined as a corresponding method step or as a feature of a method step. Similarly, aspects, which were described in connection with a method step or as a method step, also represent a description of a corresponding block or detail or feature of a corresponding device.

Depending on certain implementation requirements, exemplary embodiments of the present invention may be implemented in hardware and/or in software. A control unit may likewise be implemented in hardware or in software. The implementation may be carried out with the use of a digital storage medium, for example, a floppy disk, a DVD, a Blu-Ray disk, a CD, a ROM, a PROM, an EPROM, an EEPROM or a FLASH memory, a hard drive or another magnetic or optical memory, on which electronically readable control signals, which can interact or do interact with a programmable hardware component such that the respective method is carried out, are stored.

A programmable hardware component may be formed by a processor, a computer processor (CPU=Central Processing Unit), a graphics processor (GPU=Graphics Processing Unit), a computer, computer system, an application-specific integrated circuit (ASIC=Application-Specific Integrated Circuit), a single-chip system (SOC=System on Chip), a programmable logic element field-programmable gate array with a microprocessor (FPGA=Field Programmable Gate Array).

The digital storage medium may therefore be machine- or computer-readable. Some exemplary embodiments consequently comprise a data storage medium, which has electronically readable control signals, which are capable of interacting with a programmable computer system or with a programmable hardware component such that one of the methods being described here is executed. An exemplary embodiment is thus a data storage medium (or a digital storage medium or a computer-readable medium), on which the program is recorded for executing a method being described here.

Exemplary embodiments of the present invention may generally be implemented as a program, firmware, computer program or computer program product with a program code or as data, wherein the program code or the data acts/act such as to execute one of the methods when the program is running on a processor or on a programmable hardware component. The program code or the data may also be stored on a machine-readable storage medium or data storage medium. The program code or the data may be present, among other things, as a source code, machine code or byte code as well as another intermediate code.

Further, another exemplary embodiment is a data stream, a signal sequence or a sequence of signals, which represents/represent the program for executing one of the methods being described here. The data stream, the signal sequence or the sequence of signals may be configured, for example, such as to be transferred via data communication connection, for example, via the internet or another network. Exemplary embodiments are thus also signal sequences, which represent data and which are suitable for transmission via a network or a data communication connection, wherein the data represent the program.

A program according to one exemplary embodiment may implement one of the methods during its execution, for example, by reading storage locations or writing a datum or a plurality of data into these, as a result of which switching operations or other procedures are brought about in transistor structures, in amplifier structures or in other electrical, optical, magnetic components or components operating according to another principle of operation. Data, values, sensor values or other information may correspondingly be detected, determined or measured by a program by reading a storage location. A program may therefore detect, determine or measure variables, values, measured variables and other information by reading one or more storage locations as well as bring about, prompt or execute an action by writing to one or more storage locations as well as actuate other devices, machines and components.

The above-described exemplary embodiments represent only an illustration of the principles of the present invention. It is obvious that modifications and variations of the arrangements and details being described here will be seen by other persons skilled in the art. The present invention is therefore intended to be limited only by the scope of protection of the following patent claims rather than by the specific details that were presented here on the basis of the description and the explanation of the exemplary embodiments. While specific embodiments of the invention have been shown and described in detail to illustrate the application of the principles of the invention, it will be understood that the invention may be embodied otherwise without departing from such principles.

What is claimed is:

1. A method for controlling a device for extracorporeal blood gas exchange, wherein the device comprises a membrane as a gas-liquid barrier between a bloodstream and a gas stream, wherein the membrane makes possible a passing of carbon dioxide content over from the bloodstream into the gas stream, at least one actuator, wherein a change in a value of an operating parameter of the actuator brings about a change in a value of the carbon dioxide content, which passes over from the bloodstream into the gas stream, the method comprising the steps of:
   providing at least one control device comprising an anesthesia device and a capnometer;
   providing breathing gas information, which indicates a carbon dioxide concentration in a breathing gas;
   providing a control signal, which indicates a request for setting a value of the operating parameter;
   changing the value of the operating parameter as a function of the carbon dioxide concentration in the breathing gas;
   providing at least one minimal value, wherein in case the value of the at least one operating parameter reaches the minimal value, the value of the at least one operating parameter is retained; and
   stopping a weaning process when the value of the at least one operating parameter reaches the minimal value.

2. A method in accordance with claim 1, wherein the operating parameter has an effect on a pumping capacity of a pump that is a part of or is associated with the device.

3. A method in accordance with claim 1, wherein the operating parameter has an effect on an oxygen quantity of the gas stream.

4. A method in accordance with claim 1, further comprising the steps of:
   providing at least one comparison value, which indicates a comparison concentration; and
   changing of the value of the operating parameter as a function of the carbon dioxide concentration in the breathing gas and of the comparison concentration.

5. A method in accordance with claim 4, wherein in case the carbon dioxide concentration in the breathing gas is higher than the comparison concentration, the value of the at least one operating parameter is changed such that the value of the carbon dioxide content, which passes over from the bloodstream into the gas stream, is reduced.

6. A method in accordance with claim 4, wherein in case the carbon dioxide concentration in the breathing gas is lower than the comparison concentration, the value of the at least one operating parameter is changed such that the value of the carbon dioxide content, which passes over from the bloodstream into the gas stream, is increased.

7. A method in accordance with claim 1, further comprising the steps of:
   providing at least one piece of information, which indicates an extent of a state of ventilation of a lung; and
   providing a ventilation threshold value, wherein the retaining of the value of the at least one operating parameter is further made dependent on a comparison of the extent of the state of ventilation with the ventilation threshold value.

8. A method in accordance with claim 1, further comprising the steps of:
   providing information, which indicates an extent of inspiratory muscle activity; and
   providing an activity threshold value, wherein the retaining of the value of the at least one operating parameter is further made dependent on a comparison of the extent of the inspiratory muscle activity and on the activity threshold value.

9. A method in accordance with claim 1, further comprising the steps of:
   providing at least one first blood gas measured value, which corresponds to a first measurement time;
   providing at least one second blood gas measured value, which corresponds to a second measurement time; and
   providing an output signal as a function of the first and of the second blood gas measured value.

10. A method in accordance with claim 1, further comprising:
    providing a control unit, wherein the control unit receives the breathing gas information as input and provides the control signal as output, the at least one actuator receiving the control signal as input.

11. A device for extracorporeal blood gas exchange, the device comprising:
    a bloodstream guide area for guiding a bloodstream;
    a gas-guiding area for guiding a gas stream;
    a membrane forming a gas-liquid barrier between the bloodstream guided in the bloodstream guide area and the gas stream guided in the gas-guiding area for passing over of carbon dioxide content from the bloodstream into the gas stream;
    a data network interface;
    at least one actuator operating based on an actuator operating parameter, the actuator operating parameter having a value that determines a value of the carbon dioxide content which passes over from the bloodstream into the gas stream; and
    at least one control unit comprising a capnometer and an anesthesia device, the at least one control unit being configured:

to receive a control signal by means of the data network interface, the control signal indicating a request for setting the value of the actuator operating parameter;

to receive at least one minimal value, wherein in case the value of the at least one operating parameter reaches the minimal value, the value of the at least one operating parameter is retained;

to provide the control signal to the actuator; and to terminate a weaning process when the value of the at least one operating parameter reaches the minimal value.

12. A device for extracorporeal blood gas exchange, the device comprising:

a bloodstream guide area for guiding a bloodstream;

a gas-guiding area for guiding a gas stream;

a membrane forming a gas-liquid barrier between the bloodstream guided in the bloodstream guide area and the gas stream guided in the gas-guiding area for passing over of carbon dioxide content from the bloodstream into the gas stream;

a data network interface;

at least one actuator operating based on an actuator operating parameter, which actuator operating parameter has a value that determines a value of the carbon dioxide content which passes over from the bloodstream into the gas stream; and at least one control unit comprising a capnometer and an anesthesia device, the at least one control unit being configured:

to receive breathing gas information by means of the data network interface, which breathing gas information indicates a carbon dioxide concentration in a breathing gas;

to provide a control signal, which indicates a setting request for setting the value of the operating parameter, to the actuator;

to change the value of the operating parameter as a function of the breathing gas information indicative of the carbon dioxide concentration in the breathing gas;

to receive at least one minimal value, wherein in case the value of the at least one operating parameter reaches the minimal value, the value of the at least one operating parameter is retained; and to stop a weaning process when the value of the at least one operating parameter reaches the minimal value.

13. A control device for controlling a device for extracorporeal blood gas exchange, wherein the device for extracorporeal blood gas exchange comprises a membrane forming a gas-liquid barrier between a bloodstream and a gas stream, providing a passing over of the carbon dioxide content from the bloodstream into the gas stream and the device for extracorporeal blood gas exchange further comprises at least one actuator operating based on an actuator operating parameter, which actuator operating parameter has a value that determines a value of the carbon dioxide content which passes over from the bloodstream into the gas stream, the control device comprising:

an anesthesia device;

a capnometer;

a fluid inlet for receiving a breathing gas;

a measuring unit for determining breathing gas information, which breathing gas information indicates a carbon dioxide concentration in the breathing gas; and at least one control unit configured to:

provide a control signal, which indicates a request for setting the value of the actuator operating parameter, as a function of the carbon dioxide concentration in the breathing gas;

receive at least one minimal value, wherein in case the value of the at least one operating parameter reaches the minimal value, the value of the at least one operating parameter is retained; and stop a weaning process when the value of the at least one operating parameter reaches the minimal value.

14. A control device in accordance with claim 13, further comprising a data network interface, wherein the control unit is further configured to provide the control signal in the form of a data signal to the data network interface.

15. A control device for controlling a device for extracorporeal blood gas exchange, wherein the device for extracorporeal blood gas exchange comprises a membrane forming a gas-liquid barrier between a bloodstream and a gas stream, providing a passing over of the carbon dioxide content from the bloodstream into the gas stream and the device for extracorporeal blood gas exchange further comprises at least one actuator operating based on an actuator operating parameter, which actuator operating parameter has a value that determines a value of the carbon dioxide content which passes over from the bloodstream into the gas stream, the control device comprising:

an anesthesia device;

a capnometer;

a data network interface configured to receive a data signal, which data signal has breathing gas information, which indicates a carbon dioxide concentration in a breathing gas; and at least one control unit configured to provide a control signal, which indicates a request for setting the value of the actuator operating parameter, as a function of the carbon dioxide concentration in the breathing gas, wherein the at least one control unit receives at least one minimal value as input, wherein in case the value of the at least one operating parameter reaches the minimal value, the value of the at least one operating parameter is retained, wherein the control signal is provided in the form of a data signal to the data network interface, wherein the at least one control unit is further configured to stop a weaning process when the value of the at least one operating parameter reaches the minimal value.

\* \* \* \* \*